(12) United States Patent
Hicks

(10) Patent No.: US 7,977,090 B2
(45) Date of Patent: Jul. 12, 2011

(54) FILTRATION DEVICE FOR BIOLOGICAL SAMPLES

(75) Inventor: Richard Hicks, Surrey (GB)

(73) Assignee: Diasys Limited, Berkshire (GB)

( * ) Notice: Subject to any disclaimer, the term of this patent is extended or adjusted under 35 U.S.C. 154(b) by 887 days.

(21) Appl. No.: 11/815,575

(22) PCT Filed: Feb. 3, 2006

(86) PCT No.: PCT/GB2006/000371
§ 371 (c)(1),
(2), (4) Date: Dec. 5, 2007

(87) PCT Pub. No.: WO2006/082419
PCT Pub. Date: Aug. 10, 2006

(65) Prior Publication Data
US 2008/0213877 A1 Sep. 4, 2008

(30) Foreign Application Priority Data
Feb. 5, 2005 (GB) .................................. 0502393.2

(51) Int. Cl.
*C12M 1/00* (2006.01)
*C12M 3/00* (2006.01)
*B65C 25/08* (2006.01)
(52) U.S. Cl. .................. 435/308.1; 206/219; 435/283.1; 435/307.1
(58) Field of Classification Search ............... 435/308.1, 435/283.1, 307.1, 311; 206/219
See application file for complete search history.

(56) References Cited

U.S. PATENT DOCUMENTS

| 4,081,356 | A | | 3/1978 | Zierdt et al. |
| 4,225,423 | A | * | 9/1980 | Cotey ................................. 209/3 |
| 4,785,859 | A | * | 11/1988 | Gustavsson et al. .......... 141/313 |
| 4,859,610 | A | * | 8/1989 | Maggio ........................ 436/518 |
| 5,149,506 | A | * | 9/1992 | Skiba et al. .................... 422/557 |
| 5,624,554 | A | | 4/1997 | Faulkner et al. |
| 6,277,646 | B1 | | 8/2001 | Guirguis et al. |
| 2003/0218026 | A1 | * | 11/2003 | Moretti ..................... 222/153.06 |
| 2004/0005246 | A1 | * | 1/2004 | Efthimiadis et al. ............ 422/99 |
| 2004/0179976 | A1 | | 9/2004 | Chang |
| 2007/0102306 | A1 | * | 5/2007 | Lantos et al. ................. 206/219 |

FOREIGN PATENT DOCUMENTS

| EP | 0 298 513 | 1/1989 |
| GB | 2422794 | 9/2006 |
| WO | WO 89/00289 | 1/1989 |
| WO | WO 2005/041751 | 5/2005 |

* cited by examiner

*Primary Examiner* — Walter D Griffin
*Assistant Examiner* — Lydia Edwards
(74) *Attorney, Agent, or Firm* — Young & Thompson

(57) ABSTRACT

An open-topped container (10) is sealed by a cap (12) to the underside of which is fixed a sealed enclosure (13) containing a fixative solution. At the end of the enclosure remote from the cap is a receptacle (14) for a fecal specimen and this is surrounded by protrusions (15) of the enclosure which are ruptured by teeth (22) surrounding an uppermost filter (19) as the cap is screwed on. The fixative solution escapes from the enclosure, mixes with the fecal matter and passes through filters so that parasitic eggs are collected in the conical false bottom (23) of the container. During the final travel of the cap skirts engage the non-perforated periphery (21) of the upper filter to prevent the fixative solution flowing back into the enclosure when the container is inverted. The filtrate can be poured or pippetted out of the container through its spout (24).

9 Claims, 3 Drawing Sheets

FILTRATION DEVICE FOR BIOLOGICAL SAMPLES

This invention relates to a filtration device for biological samples, particularly but not exclusively samples of faeces which are to be filtered to separate parasitic eggs.

At present a patient is provided with a specimen jar containing a diluted fixative such as formalin and asked to place in it approximately 5 g of faecal matter. The fixative kills the parasites and "freezes" the eggs such that the morphology of the sample is maintained. Having sealed the specimen jar the patient returns it to his doctor who forwards it to a laboratory dedicated to parasite recovery and identification. At the laboratory the sample is transferred to a collection tube with filter meshes, typically a 50 ml collection tube with 1200 um and 600 um filter meshes, and subsequently to a centrifuge tube, typically a 15 ml centrifuge tube with 300 um and 200 um filter meshes. The parasite eggs are typically no bigger than 150 um long and so pass to the bottom of the centrifuge tube when spun, where they can be drawn off by pipette and placed on a glass slide for microscope examination.

This regime requires three separate devices and exposure of the laboratory technician or other operative to the sample on three separate occasions as it is transferred from one device to another. To avoid the risk of infection the operative should wear protective clothing, such as a mask and gloves.

A principal object of the present invention is to simplify the procedure and reduce the exposure of an operative to the sample. A single, sealed device is provided in which the sample is contained, dissolved and filtered. In most cases because of the way in which the device is used it may not be necessary to transfer the filtrate to a centrifuge tube.

In accordance with the present invention there is provided a filtration device for biological samples, the device comprising an open-topped container, at least one filter member spanning the interior of the container in spaced relation to said top, and a cap for sealing the open top of the container, there being fixed to the underside of the cap to project into the container a sealed enclosure for a fluid having at its distal end remote from the cap a receptacle for a biological sample, and there being provided in the container means which will rupture the enclosure when the cap is fully received by the container.

Preferably the cap makes a screw-threaded engagement with the container, said rupturing means being adapted to rupture the enclosure during a final part of the travel of the cap as it is screwed onto the container.

The screw-threaded engagement is preferably non-reversible such that after engagement with the container the cap cannot be removed by counter-rotation.

In a preferred embodiment of the invention said one filter member has a non-perforated peripheral region provided with upstanding teeth which will rupture the distal end of the enclosure around the receptacle when the cap is fully received by the container.

A skirt around the receptacle is preferably provided which projects from the distal end of the enclosure to engage said non-perforated peripheral region of said one filter member when the cap is fully received by the container thereby to prevent fluid which has flowed out of the ruptured enclosure through said one filter member from re-entering the enclosure.

The distal end of the enclosure may have an annular array of circumferentially separated protrusions aligned with the teeth when the cap engages the container, the arrangement being such that as the cap is fully received by the container the teeth will move between the protrusions and rupture the same as the cap is rotated.

The protrusions may take the form of part-cylindrical protrusions having axes radial with respect to the cap.

The interior of the container is preferably spanned by a second filter member spaced from said one filter member away from the open top of the container, said second filter member having a finer mesh size than said one filter member.

Each of said filter members may be cup-shaped.

The container may be provided interiorly with a conical false bottom tapering away from the open top of the container and may have an outwardly projecting spout the bottom of which is continuous in a straight line with the upper surface of the cone such that parasitic matter collected at the apex of the cone can be reached by a pipette inserted through the opening of the spout.

Preferred embodiments of the invention will now be described by way of non-limitative example with reference to the accompanying drawings, in which.

Figure 1:
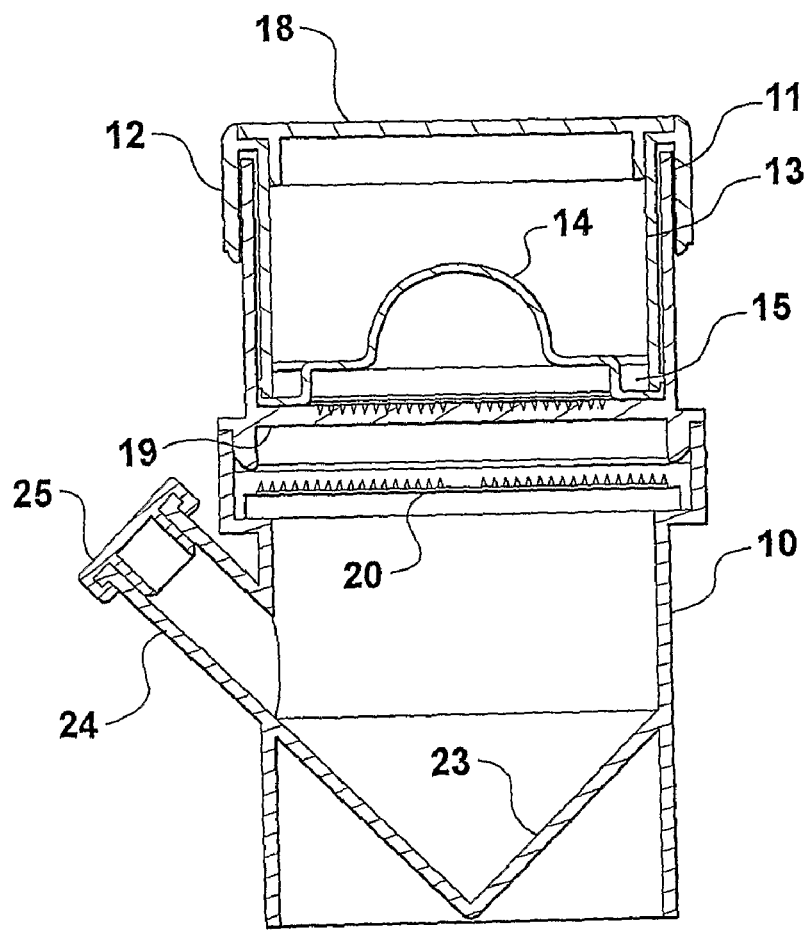
FIG. 1 is a sectional elevation of a device in accordance with the invention.

The device illustrated in FIG. 1 comprises a container 10 open at its top 11 and sealed by a cap 12. The cap makes a screw-threaded engagement with the top of the container and this is of the non-reversible kind which is used to "child proof", for example, bottles of bleach except that such known "child proofing" can be overcome by squeezing the cap when it is desired to remove it. The present device is a "one use only", disposable item and the cap is rigid so that after the screw-threads are engaged it cannot be removed.

Figure 4:
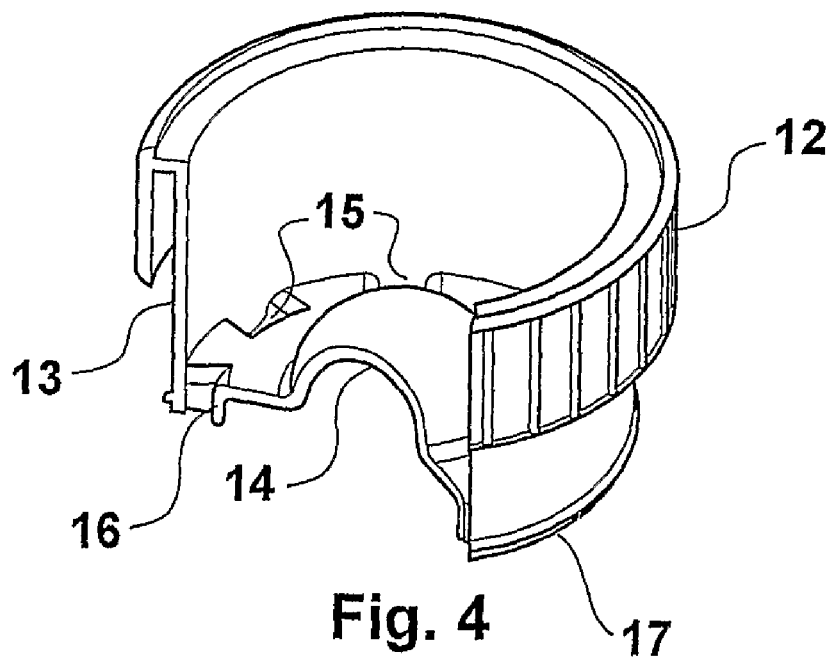

Fixed to the underside of the cap 12 is a sealed enclosure 13 filled with a fixative solution. Central to the distal end of the enclosure 13 remote from the cap 12 is a dome-like receptacle 14. Around this the base of the enclosure 13 has been deformed to provide an annular array of circumferentially spaced part-cylindrical protrusions 15. The distal end of the enclosure 13 terminates in skirts 16 and 17 projecting slightly beyond the protrusions 15. In the view of FIG. 4 the cap and enclosure have been cut away and the top 18 of the enclosure has been removed to reveal the interior of the enclosure and the upper sides of the protrusions 15.

Figure 2:
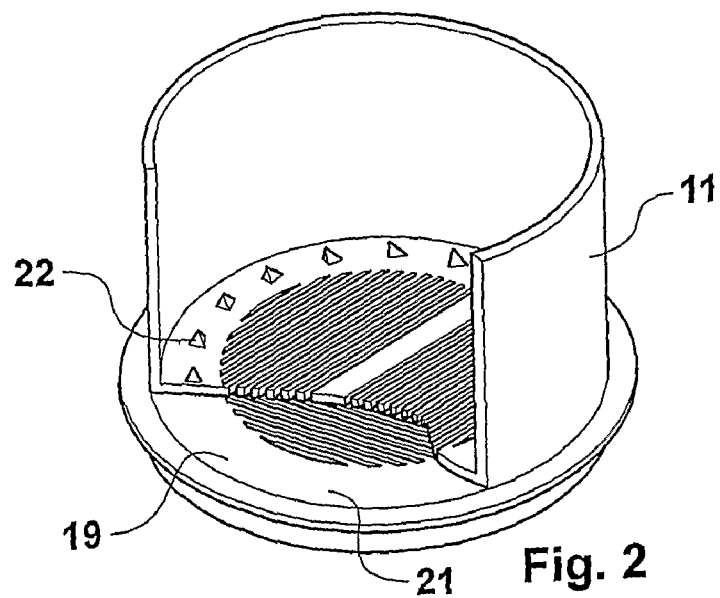
FIGS. 2, 3 and 4 illustrate on a larger scale components of the device of FIG. 1.
Figure 3:
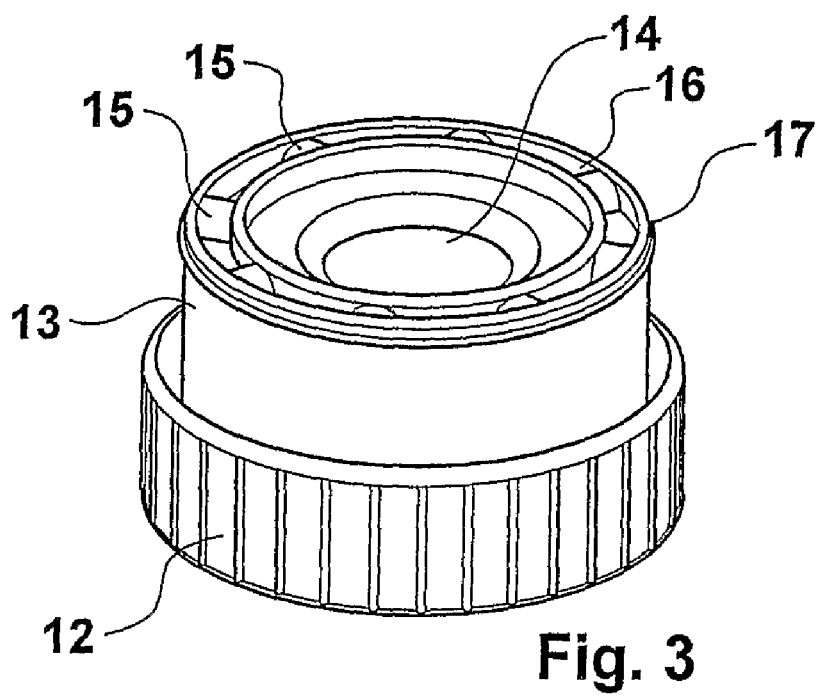

Spanning the interior of the container 10 in spaced relation to its top 11 and to one-another are a first filter member 19 and a second filter member 20. The filter member 19 is a 400 um pre-filter and the second filter member 20 is a 200 um cleaning filter. As is most clear from FIG. 2 the filter member 19 has a non-perforated peripheral region 21 formed with upstanding teeth 22. As the cap 12 is screwed onto the container 10 these teeth 22 will pass between the protrusions 15 and rupture them, causing the fixative solution to run out of the enclosure 13 and through the filters 19 and 20. However in the final position of the cap 12 the skirts 16 and 17 will abut the non-perforated region 21 of the filter member 19 so that the fixative solution cannot run back into the enclosure 13 when the device is inverted.

The container 10 has a conical false bottom 23 for concentrating at its apex the parasitic material which has passed through the filters 19 and 20. The container 10 also has a projecting spout 24 and the bottom of this is in a straight line with the cone 23 to facilitate the insertion of a pipette through the spout 24 to collect material from the apex of the cone. The spout 24 can also be used for pouring the filtered material out of the container 10 and has a stopper 25.

Figure 5:
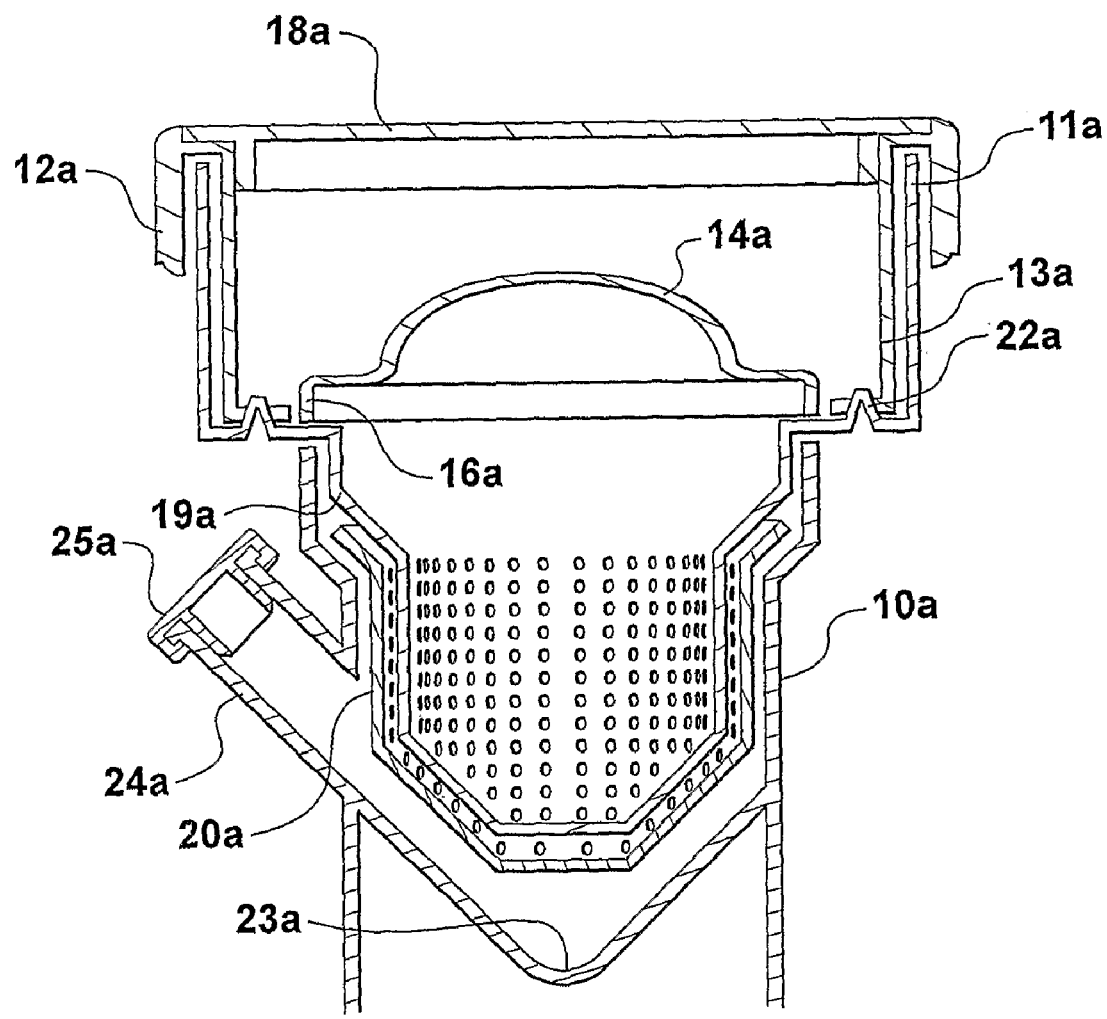
FIG. 5 is a sectional elevation of an alternative device in accordance with the invention.

The device illustrated in FIG. 5 is similar to that of FIGS. 1-4 and like parts have the same reference numerals but with the suffix A. The differences are that the filter members 19A and 20A are cup-shaped instead of flat, thus increasing their filtering areas.

The intended use of both devices is the same. A patient is given the device with the cap 12 or 12A separated from the container 10 or 10A. Holding the cap upside down as in FIG. 3 a faecal sample is placed in the receptacle 14 or 14A and then the top 11 or 11A of the container is engaged with the screw-threads of the cap. As the cap is screwed onto the container first the teeth 22 or 22A rupture the protrusions 15 or 15A, so that with the container 10 or 10A held in the upright position of FIG. 1 the fixative solution escapes from the enclosure 13 or 13A, mixes with the faecal material and passes through the filters and then, during the final travel of the cap, the skirts 16 and 17 or 16A and 17A abut the non-perforated peripheral region of the upper filter member to prevent the fixative solution passing back into the enclosure 13 or 13A if the container 10 or 10A is again inverted. The patient will be encouraged to shake the sealed container 10 or 10A to ensure that the faecal specimen is fully separated from the receptacle 14 or 14A and dissolved in the fixative solution. In any event the sealed container 10 or 10A will be shaken as it travels to the doctor and to the laboratory over a fairly lengthy period before a laboratory technician is ready to remove the filtered material from the cone 23 or 23A. It is intended that in most cases it will not be necessary to centrifuge the filtered material. It can either be poured out through the spout 24 or 24A or removed by inserting a pipette through the spout.

The invention claimed is:

1. A filtration device for biological samples, the device comprising an open-topped container and a cap for closing the open top of the container, there being fixed to the underside of the cap to project into the container when the container is closed a sealed enclosure for a fluid, means being provided within the container at a position where it will rupture the enclosure as the container is fully closed by the cap thereby discharging the fluid into the container.

2. A filtration device for biological samples, the device comprising an open-topped container and a cap for closing the open top of the container by making a screw-threaded engagement therewith, there being fixed to the underside of the cap to project into the container when the container is closed a sealed enclosure for a fluid, the enclosure having at its distal end peripheral, circumferentially spaced protrusions and the interior of the container being provided with teeth at a position such that they will rupture the protrusions during final rotation of the cap to its closing position thereby discharging the fluid into the container.

3. A filtration device as claimed in claim 2, wherein the teeth upstand from the imperforate peripheral region of a member spanning the interior of the container at a position spaced from the top of the container approximately equal to the depth of the enclosure, the distal end of the enclosure having at least one skirt projecting therefrom beyond said protrusions, the arrangement being such that when the cap is in its final, closing position said skirt or skirts will contact said imperforate peripheral region of said member to prevent fluid flowing back into the cap if the container is inverted.

4. A filtration device as claimed in claim 3, wherein the distal end of the enclosure is formed as a receptacle for a biological specimen and wherein a central region of said member within its imperforate peripheral region is a filter.

5. A filtration device as claimed in claim 4, wherein the interior of the container is spanned by a second filter spaced from the filter of said member away from the top of the container, said second filter having a finer mesh size than that of the filter of said member.

6. A filtration device as claimed in claim 5, wherein each of the filters is cup-shaped.

7. A filtration device as claimed in claim 4, wherein the container is provided interiorly with a conical false bottom tapering away from the top of the container and has an outwardly projecting spout the bottom of which is continuous in a straight line with the upper surface of the cone such that parasitic matter collected at the apex of the cone can be reached by a pipette inserted into the container through the spout.

8. A filtration device for biological samples, the device comprising an open-topped container and a cap for closing the open top of the container by making a screw-threaded engagement therewith, there being fixed to the underside of the cap to project into the container when the container is closed a sealed enclosure for a fluid having at its distal end a central depression to serve as a receptacle for a biological sample, a filter member spanning the interior of the container at a position spaced from said open top approximately equal to the depth of the enclosure, the filter member having an imperforate peripheral region provided with an array of circumferentially separated teeth, the enclosure having at its distal end peripheral, circumferentially spaced protrusions, the arrangement being such that the teeth will pass between and rupture the protrusions during final rotation of the cap to its closing position thereby discharging the fluid into the container.

9. A filtration device as claimed in claim 8, wherein the enclosure has at its distal end alongside the protrusions at least one skirt which will contact the imperforate peripheral region of said filter member as the cap is rotated to its final, closing position thereby preventing the fluid from flowing back into the enclosure if the container is inverted.

* * * * *